US010610647B2

(12) United States Patent
Felsovalyi et al.

(10) Patent No.: US 10,610,647 B2
(45) Date of Patent: *Apr. 7, 2020

(54) SYRINGE ASSEMBLY WITH PIVOTING PLUNGER AND INTEGRAL TIP GUARD

(71) Applicant: Becton Dickinson France, Le Pont-de-Claix (FR)

(72) Inventors: Flora Felsovalyi, Bloomingdale, NJ (US); Eric Schiller, Kinnelon, NJ (US)

(73) Assignee: Becton Dickinson France, Le Pont-de-Claix (FR)

( * ) Notice: Subject to any disclaimer, the term of this patent is extended or adjusted under 35 U.S.C. 154(b) by 239 days.

This patent is subject to a terminal disclaimer.

(21) Appl. No.: 15/795,789

(22) Filed: Oct. 27, 2017

(65) Prior Publication Data

US 2018/0043100 A1 Feb. 15, 2018

Related U.S. Application Data

(63) Continuation of application No. 12/859,544, filed on Aug. 19, 2010, now Pat. No. 9,821,119.

(Continued)

(51) Int. Cl.
*A61M 5/31* (2006.01)
*A61M 5/315* (2006.01)
(Continued)

(52) U.S. Cl.
CPC .......... *A61M 5/31511* (2013.01); *A61M 5/28* (2013.01); *A61M 5/31515* (2013.01);
(Continued)

(58) Field of Classification Search
CPC ...... A61M 2005/31518; A61M 5/3202; A61M 5/3216
See application file for complete search history.

(56) References Cited

U.S. PATENT DOCUMENTS

| 622,848 A | 4/1899 | Geer |
|---|---|---|
| 1,008,078 A | 11/1911 | Schroeder |

(Continued)

FOREIGN PATENT DOCUMENTS

| DE | 20016069 U1 | 12/2000 |
|---|---|---|
| EP | 0643977 A1 | 3/1995 |

(Continued)

*Primary Examiner* — William R Carpenter
(74) *Attorney, Agent, or Firm* — The Webb Law Firm

(57) ABSTRACT

The invention provides a syringe assembly comprising a syringe barrel having an inside surface defining a chamber, an open proximal end, and a distal end having an opening therethrough. An elongated plunger rod extends between a first end and a second end, with a cap or guard disposed on the first end of the plunger rod. A plunger head extends within the chamber of the syringe barrel, and is adapted for slidable movement within the syringe barrel between the proximal end and the distal end, with the second end of the plunger rod connected with the plunger head through a pivotable connection. The plunger rod is adapted to pivot with respect to the plunger head between a first position in which the guard is adjacent the distal end of the syringe barrel and a second position in which the plunger rod is in general axial alignment with the syringe barrel, and is further adapted for axial movement so as to cause sliding movement of the plunger head through the syringe barrel to expel contents thereof.

34 Claims, 12 Drawing Sheets

Related U.S. Application Data

(60) Provisional application No. 61/235,817, filed on Aug. 21, 2009.

(51) Int. Cl.
*A61M 5/28* (2006.01)
*A61M 5/50* (2006.01)

(52) U.S. Cl.
CPC ............... *A61M 2005/3104* (2013.01); *A61M 2005/31518* (2013.01); *A61M 2005/5073* (2013.01)

(56) References Cited

U.S. PATENT DOCUMENTS

| | | | |
|---|---|---|---|
| 1,512,294 A | | 10/1924 | Marcy |
| 1,678,991 A | | 7/1928 | Marschalek |
| 1,715,771 A | | 6/1929 | MacGregor |
| 1,737,857 A | | 12/1929 | MacGregor |
| 1,971,687 A | | 8/1934 | Kratz |
| 2,390,246 A | | 12/1945 | Folkman |
| 2,461,481 A | | 2/1949 | Roehr |
| 2,561,233 A | | 7/1951 | Ryan et al. |
| 2,630,804 A | | 3/1953 | Mende |
| 2,671,450 A | | 3/1954 | Dann |
| 2,672,142 A | | 3/1954 | Melton |
| 2,672,868 A | | 3/1954 | Hickey |
| 2,673,562 A | | 3/1954 | Ivadinger |
| 2,773,500 A | | 12/1956 | Young |
| 2,871,858 A | | 2/1959 | Dann et al. |
| 3,495,591 A | | 2/1970 | Wilson |
| 3,680,559 A | * | 8/1972 | Gorbahn ............. A61M 5/3129 604/193 |
| 4,011,868 A | * | 3/1977 | Friend ................ A61M 5/31511 604/194 |
| 4,221,218 A | | 9/1980 | Pfleger |
| 4,581,023 A | * | 4/1986 | Kuntz ..................... A61M 5/24 604/234 |
| 4,664,259 A | * | 5/1987 | Landis ................ A61M 5/3216 206/364 |
| 5,067,947 A | | 11/1991 | Volk et al. |
| 5,086,780 A | | 2/1992 | Schmitt |
| 5,098,382 A | | 3/1992 | Haber et al. |
| 5,135,507 A | | 8/1992 | Haber et al. |
| 5,135,511 A | | 8/1992 | Houghton et al. |
| 5,176,657 A | | 1/1993 | Shields |
| 5,242,422 A | | 9/1993 | Schneberger et al. |
| 5,279,588 A | * | 1/1994 | Nicoletti ........... A61M 25/0637 604/250 |
| 5,411,492 A | | 5/1995 | Sturman et al. |
| D366,698 S | | 1/1996 | Stiehl et al. |
| 5,573,514 A | | 11/1996 | Stiehl et al. |
| 5,700,246 A | | 12/1997 | Stiehl et al. |
| 6,003,556 A | | 12/1999 | Brugger et al. |
| 6,719,735 B1 | | 4/2004 | Gammon |
| 7,569,036 B2 | | 8/2009 | Domkowski et al. |
| 2003/0040706 A1 | * | 2/2003 | Kuracina ............. A61M 5/158 604/116 |
| 2005/0154354 A1 | | 7/2005 | Kawasaki et al. |
| 2005/0251096 A1 | | 11/2005 | Armstrong et al. |
| 2006/0229568 A1 | | 10/2006 | Koopman |
| 2007/0135764 A1 | * | 6/2007 | Chen ..................... A61M 5/322 604/110 |

FOREIGN PATENT DOCUMENTS

| | | | |
|---|---|---|---|
| EP | 0664137 A2 | | 7/1995 |
| WO | 97/29798 A1 | | 8/1997 |
| WO | WO-9729798 A1 | * | 8/1997 ......... A61M 5/31511 |

* cited by examiner

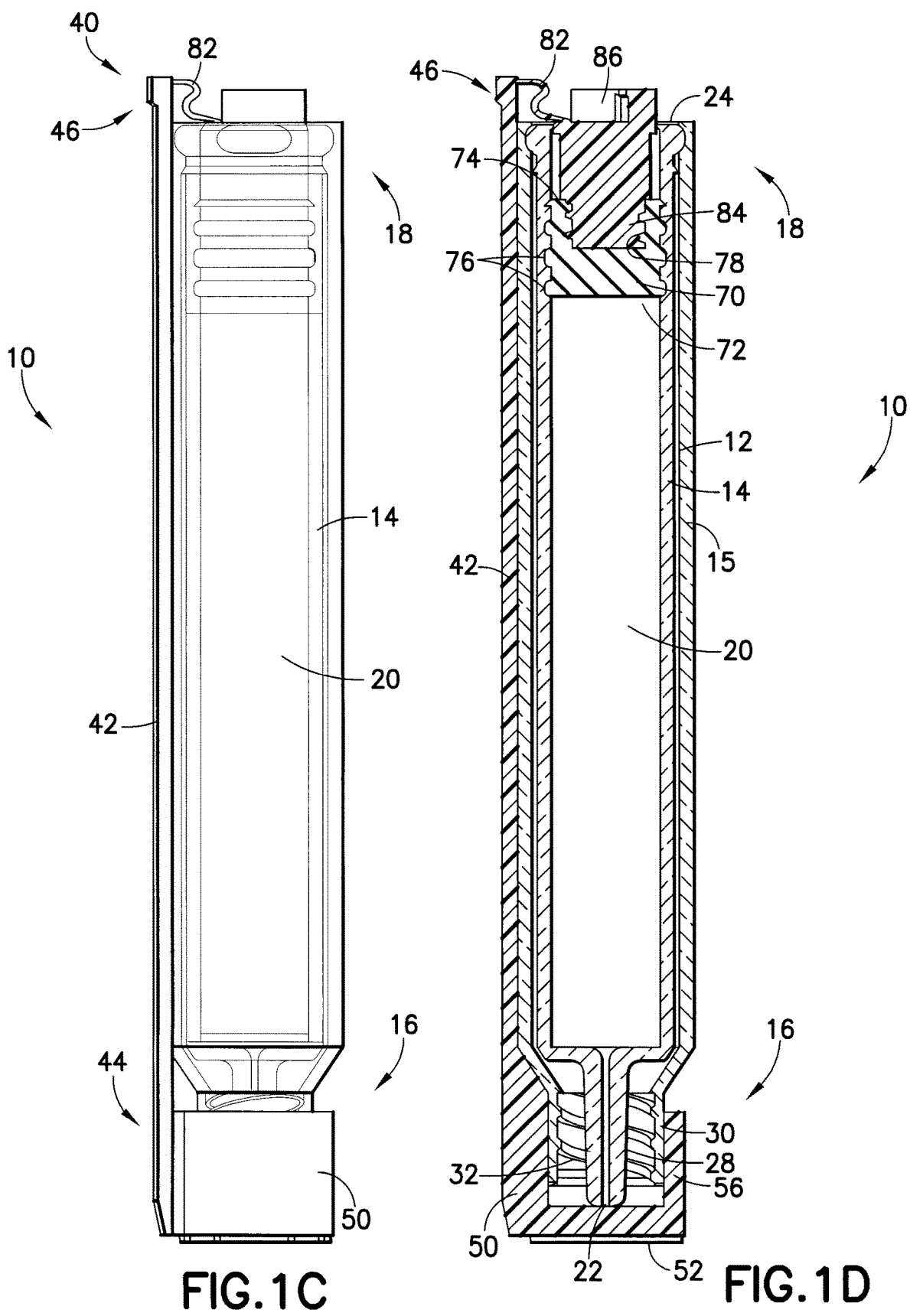

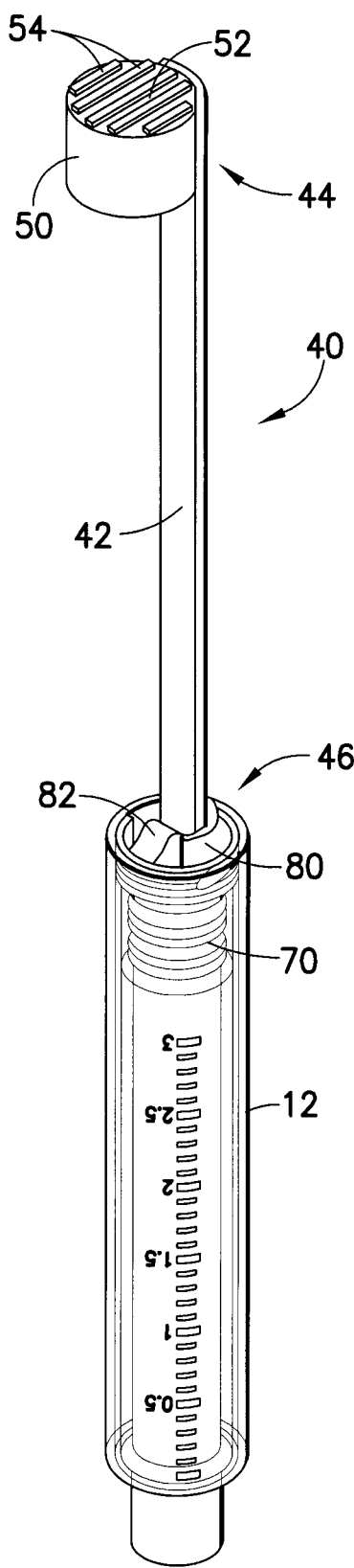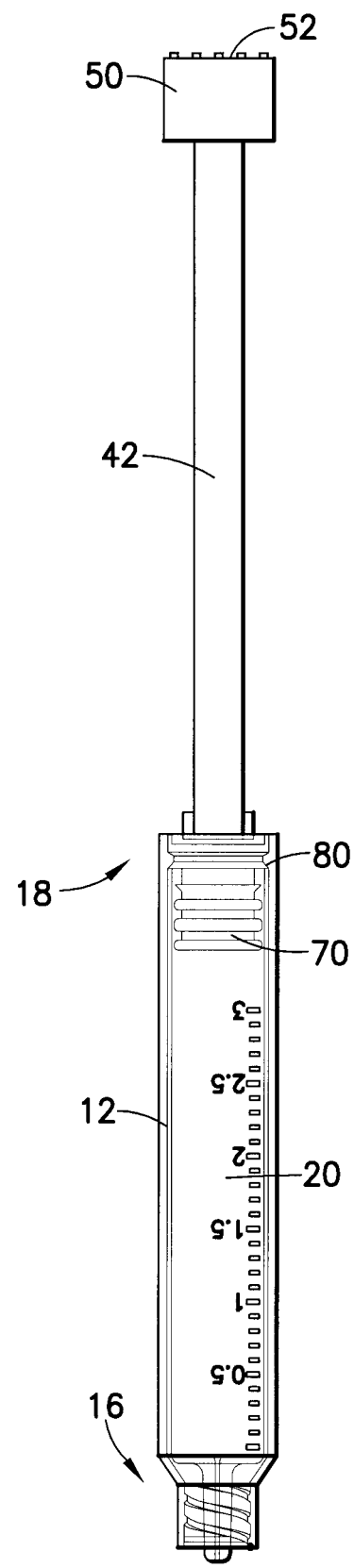
FIG.2A
FIG.2B

SYRINGE ASSEMBLY WITH PIVOTING PLUNGER AND INTEGRAL TIP GUARD

CROSS REFERENCE TO RELATED APPLICATION

This application is a continuation of U.S. application Ser. No. 12/859,544 entitled "Syringe Assembly with Pivoting Plunger and Integral Tip Guard" filed Aug. 19, 2010, which claims priority to U.S. Provisional Application No. 61/235,817 entitled "Syringe Assembly with Pivoting Plunger and Integral Tip Guard" filed Aug. 21, 2009, the entire disclosures of each of which are hereby incorporated by reference.

BACKGROUND OF THE INVENTION

Field of the Invention

The present invention is directed to a syringe assembly adapted for dispensing and delivery of a fluid. More particularly, the present invention is directed to a syringe assembly such as a hypodermic syringe having a reduced profile prior to use, and further includes an integral tip guard for maintaining sterility.

Related Technology

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to aspirate or fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depressing of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Packaging of such pre-filled syringes, however, tends to be bulky. A pre-filled syringe is typically packaged with the opening at the front end of the barrel including a separate cap thereover and with the plunger rod retracted out of the back end of the syringe barrel, with the fluid pre-filled within the syringe barrel. Such packaging creates an elongated package that can be awkward for shipping and storage.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or of the contents of these syringes. The space within these controlled storage locations is often limited, thus there is a need for a syringe assembly that has a smaller packing footprint, to reduce the storage space required for containing the syringe. It is also desirable to produce syringes that are uniform in terms of an outer surface shape to allow for stacking of these syringes within the storage cabinet.

SUMMARY OF THE INVENTION

The present invention provides a syringe assembly having a reduced profile prior to use, thereby occupying less space than a conventional syringe and providing a mechanism for reduced overall size and for efficient packaging that reduces or eliminates excess waste and prevents premature actuation. Further, the syringe assembly of the present invention includes an integrated tip guard so as to maintain sterility of the syringe tip prior to use.

In one embodiment, the invention provides a syringe assembly comprising a syringe barrel having an inside surface defining a chamber, an open proximal end, and a distal end having an opening therethrough. An elongated plunger rod extends between a first end and a second end, with a cap or guard disposed on the first end of the plunger rod. A plunger head extends within the chamber of the syringe barrel, and is adapted for slidable movement within the syringe barrel between the proximal end and the distal end, with the second end of the plunger rod connected with the plunger head through a pivotable connection. The plunger rod is adapted to pivot with respect to the plunger head between a first position in which the guard is adjacent the distal end of the syringe barrel, and a second position in which the plunger rod is in general axial alignment with the syringe barrel, and is further adapted for axial movement so as to cause sliding movement of the plunger head through the syringe barrel.

BRIEF DESCRIPTION OF THE DRAWINGS

FIG. 1C is a side plan view of the syringe assembly of FIG. 1A.

FIG. 1D is a side cross-sectional view of the syringe assembly of FIG. 1A.

FIG. 2A is a perspective view of the syringe assembly of FIG. 1A shown after dispensing of the medication after use.

FIG. 2B is a front plan view of the syringe assembly of FIG. 2A after use.

DETAILED DESCRIPTION

Figure 1A:
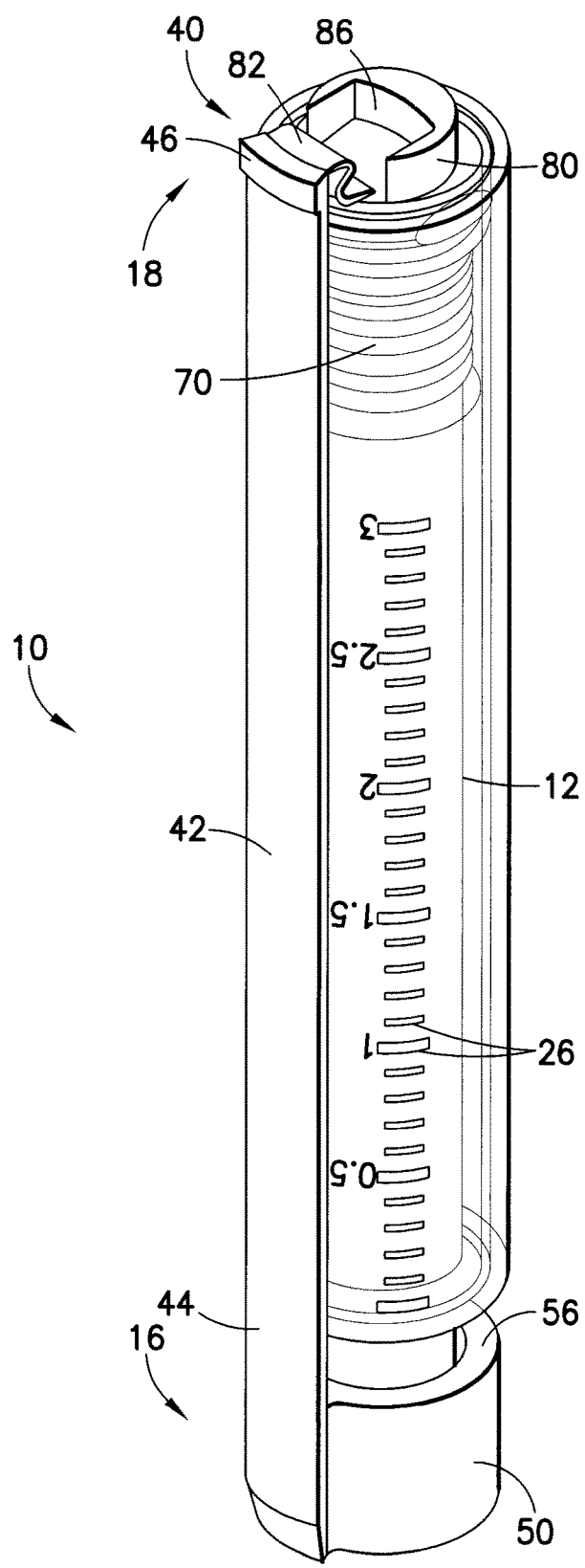
FIG. 1A is a perspective view of a syringe assembly in one embodiment of the present invention shown in a pre-filled state prior to use.
Figure 1B:
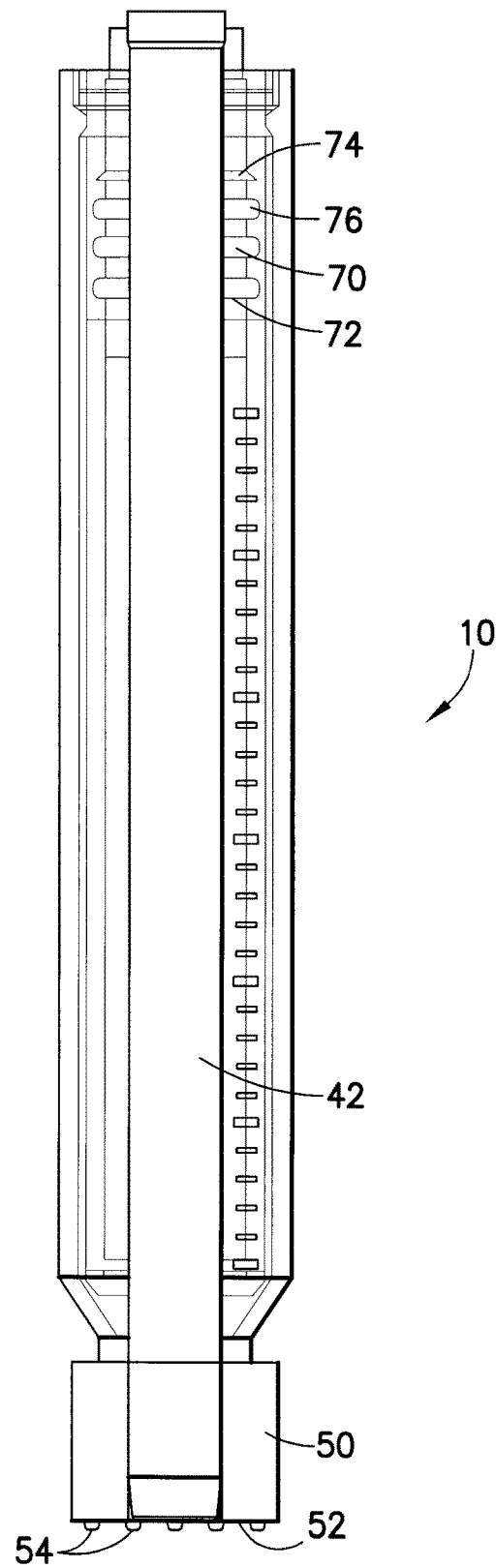
FIG. 1B is a front plan view of the syringe assembly of FIG. 1A.
Figure 2C:
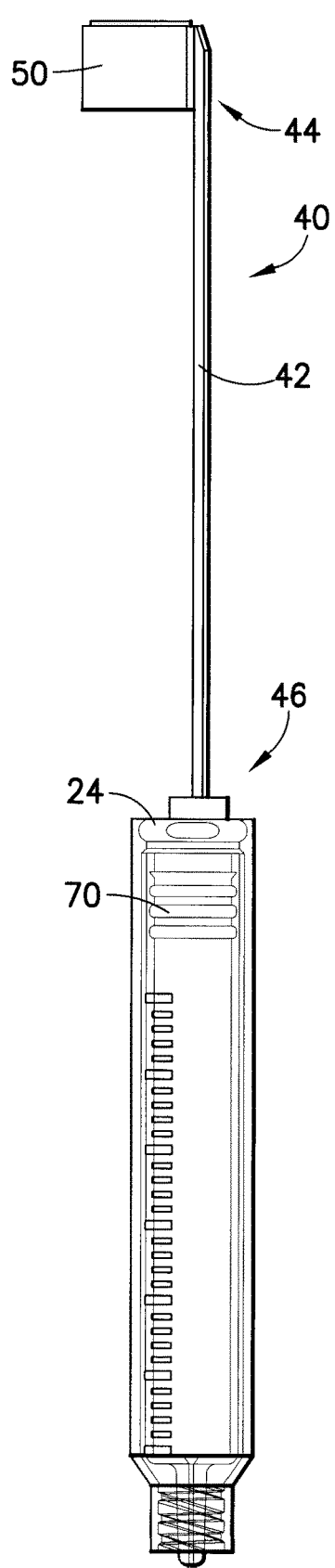
FIG. 2C is a side plan view of the syringe assembly of FIG. 2A after use.
Figure 2D:
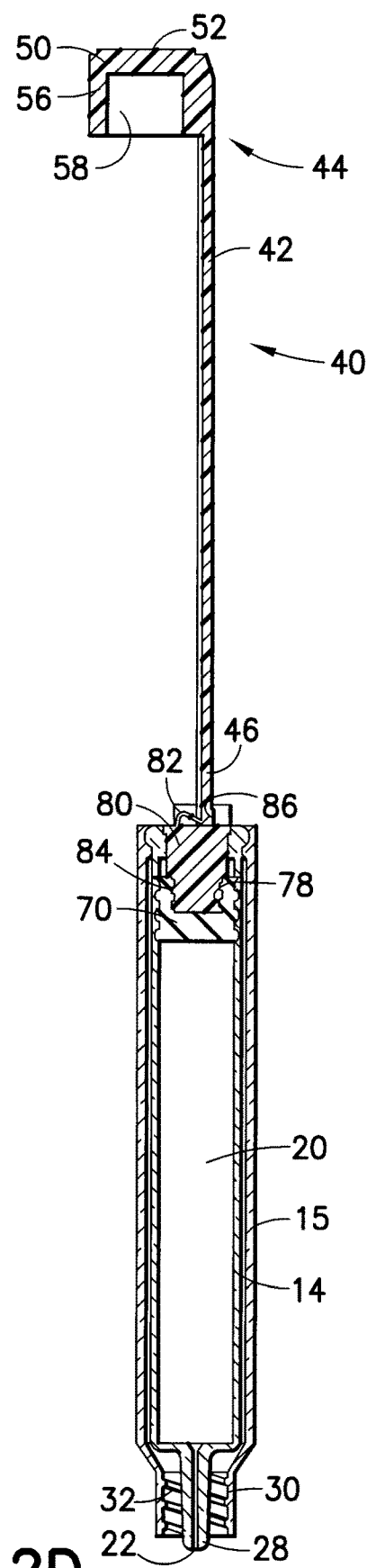
FIG. 2D is a side cross-sectional view of the syringe assembly of FIG. 2A after use.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

Reference is now made to FIGS. 1A-1D and 2A-2D, which depict a syringe assembly, generally indicated as 10, adapted for dispensing and delivery of a fluid. Syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

Syringe assembly 10 includes syringe barrel 12 defined by barrel wall 14 extending between a forward or distal end 16 and a rearward or proximal end 18, thereby defining interior chamber 20 of syringe barrel 12. Syringe barrel 12 may be in the general form of an elongated cylindrical barrel as is known in the art for the general shape of a hypodermic syringe, although other forms for containing a fluid for delivery are also contemplated by the present invention. Forward end 16 of syringe barrel 12 includes an outlet opening 22, and rearward end 18 is generally open-ended at rearward opening 24, but is intended to be closed off to the external environment, as will be discussed in more detail herein. Syringe barrel 12 may include markings, such as graduations 26 on the wall thereof, for providing an indication as to the level or amount of fluid contained within syringe barrel 12. Such markings may be provided on the external wall, the internal wall, or integrally formed or otherwise within the wall of syringe barrel 12. Alternatively or in addition thereto, the markings may provide a description of the contents of the syringe, or other identifying information, as may be known in the art.

As noted, forward end 16 of syringe barrel 12 includes an outlet opening 22. The profile of outlet opening 22 may be adapted for engagement with a separate device, such as a needle assembly or IV connection assembly, and therefore may include a mechanism for such engagement, such as an engagement mechanism that generally extends from the forward end 16 of syringe barrel 12. For example, a generally tapered luer tip 28, for engagement with a separate tapered luer mating surface (not shown) of such a separate device for attachment therewith may be provided. In addition, a mechanism for locking engagement therebetween may also be provided, such as a luer collar or luer lock 30 including interior threads 32. Such luer connections and luer locking mechanisms are well known in the art.

Figure 9:
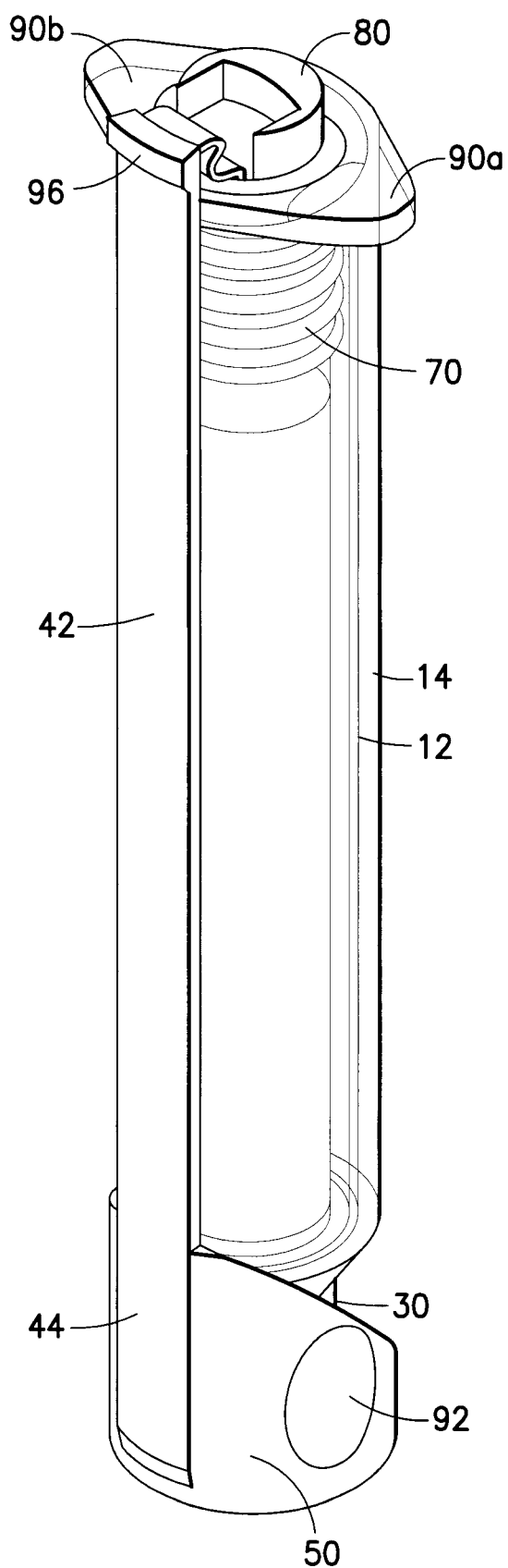
FIG. 9 is a perspective view of a syringe assembly in a further embodiment shown in a pre-filled state prior to use.
Figure 10:
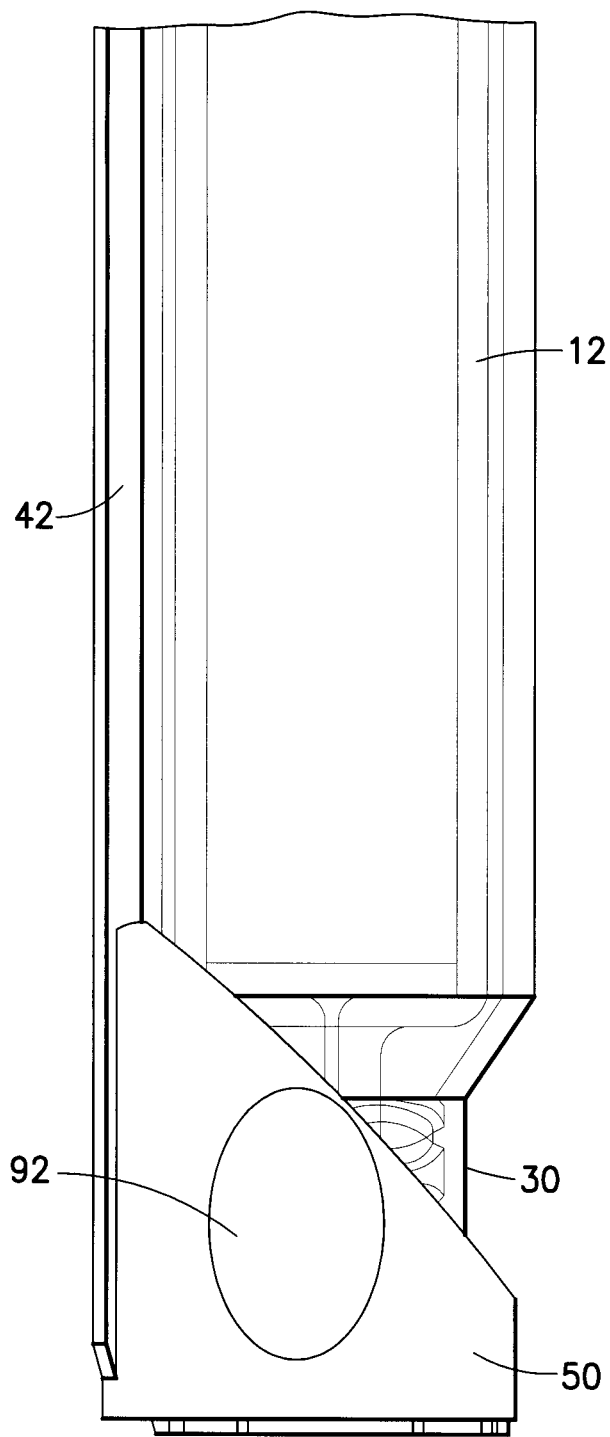
FIG. 10 is an enlarged side plan view of the syringe assembly of FIG. 9.

Syringe barrel 12 may further include a finger grasping surface, such as finger flanges 90a and 90b, shown in the embodiment set forth in FIGS. 9-10. Finger flanges 90a, 90b provide finger support surfaces for a user during use of syringe assembly 10 for expelling the contents thereof, as will be described in further detail herein.

Syringe assembly 10 further includes a plunger assembly 40, a portion of which is adapted to be disposed at least partially within syringe barrel 12. Plunger assembly 40 provides a mechanism for dispensing fluid contained within the interior chamber 20 of syringe barrel 12. In particular, plunger assembly 40 includes a plunger rod 42, which provides a mechanism for extension of a stopper portion such as plunger head 70 disposed within interior chamber 20 for dispensing the contents of the syringe assembly, as will be discussed further herein.

Plunger rod 42 is a generally elongated structure extending between first end 44 and second end 46. As will be described in greater detail herein, plunger rod 42 is adapted for positioning adjacent along the outside of wall 14 of syringe barrel 12 with first end 44 adjacent forward end 16 of syringe barrel 12 in a first position, and is further adapted for pivotal movement to a second position with first end 44 extending axially beyond rearward end 18 of syringe barrel 12 with the elongated structure of plunger rod 42 in general axial alignment with syringe barrel 12 at rearward end 18 thereof. Plunger rod 42 may further include a magnification member (not shown) which may be disposed along the elongated portion of plunger rod 42 so as to magnify the markings, such as graduations 26, on the wall of syringe barrel 12 when plunger rod 42 is positioned along the outside of wall 14 of syringe barrel 12, allowing a user to more easily identify the volume of liquid contained in syringe barrel 12 before or after use.

Figure 3:
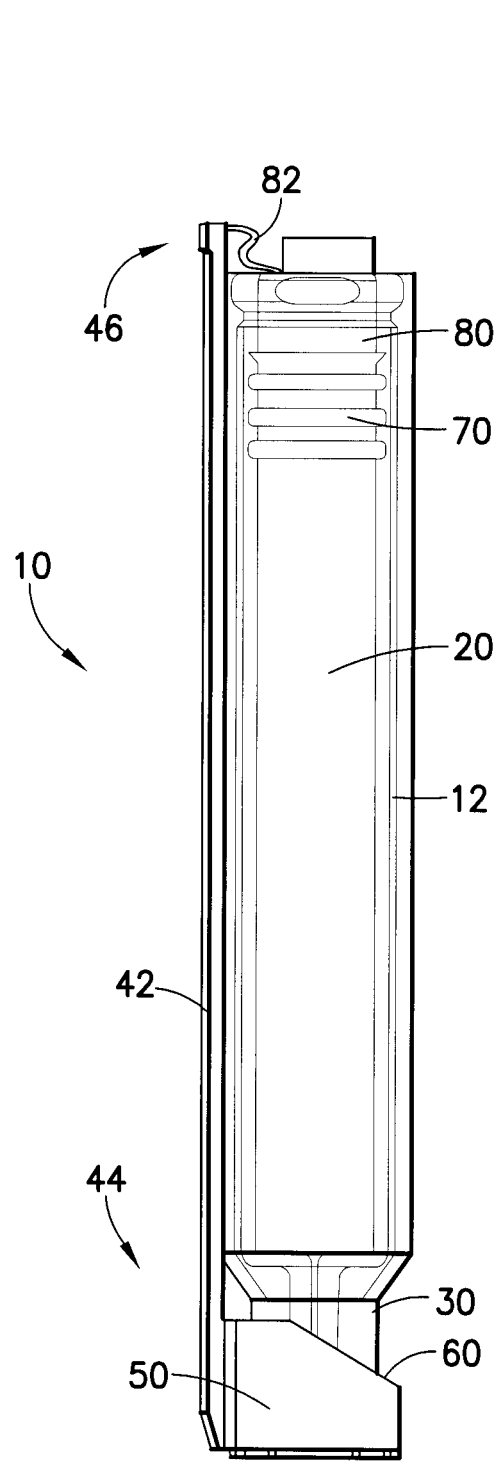
FIG. 3 is a side plan view of a syringe assembly having features similar to that of FIG. 1A shown in a pre-filled state prior to use.
Figure 4:
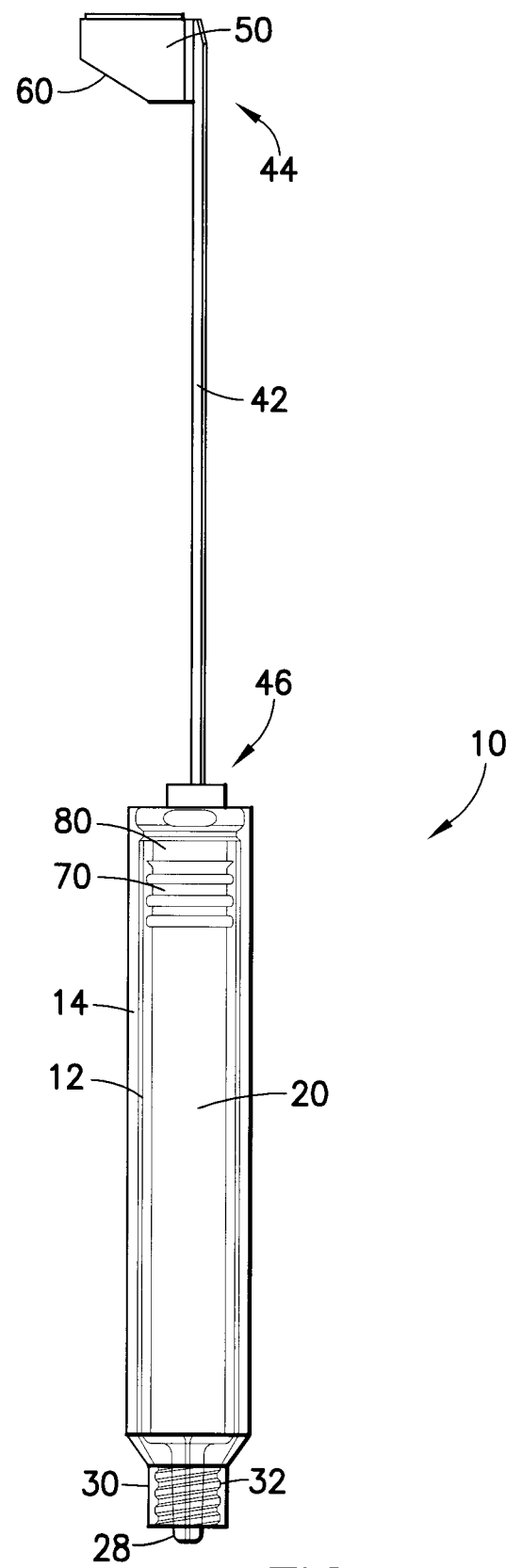
FIG. 4 is a side plan view of the syringe assembly of FIG. 3 shown after dispensing of the medication after use.

First end 44 of plunger rod 42 may be provided with a mechanism for engagement with outlet opening 22 of syringe barrel 12 for maintaining sterility thereof. Such sterility can be accomplished by, for instance, positioning the mechanism or a portion thereof so as to cover the outlet opening 22, thereby preventing contaminants that may be present in the external environment from contacting or entering outlet opening 22. Other portions of the syringe assembly 10 disposed at or near forward end 16 of syringe barrel 12, including an engagement mechanism such as luer tip 28 and/or luer lock 30, may also be shielded from the external environment by way of the above-mentioned mechanism. For example, a cap such as tip guard 50 may be provided at first end 44. Tip guard 50 may be integrally formed with plunger rod 42, or may be a separate structure that is attached to first end 44 of plunger rod 42. Tip guard 50 includes a finger or thumb pad 52 extending along an outer surface thereof, which may be provided with ribs 54 for providing a tactile surface for a user. Tip guard 50 further includes an annular skirt 56 forming a cylindrical opening 58 therein. Cylindrical opening 58 includes an inner diameter that is substantially the same as the outer diameter of the annular skirt formed by luer lock 30, and is adapted to surround luer lock 30 in a sealing engagement. Cylindrical opening 58 may further include a soft material or an elastomeric material for providing sealing engagement with luer lock 30. In a further modification of this embodiment, annular skirt 56 of tip guard 50 may further include a cut-away section 60, as shown in FIGS. 3-4. Cut-away 60 provides tip guard 50 with a reduced profile about a portion of annular skirt 56 so as to provide for easier removal of tip guard 50 from luer lock 30. In a further embodiment, annular skirt 56 of tip guard 50 may be split into two sections, such that annular skirt 56 snap fits around forward end 16 at the luer collar of luer lock 30.

In a further embodiment, tip guard 50 may further be provided with finger recesses, such as finger recesses 92 shown in the embodiment of FIGS. 9 and 10. Finger recesses 92 are designed so as to accommodate a user's fingers for a tactile surface for grasping and moving of tip guard 50 relative to forward end 16 of syringe barrel 12.

The second end 46 of plunger rod 42 is adapted for interconnection with plunger head 70. Plunger head 70 includes a distal face at first end 72 and a proximal face at second end 74. Plunger head 70 is in contact with the internal surface of syringe barrel wall 14, and may include one or more annular ribs extending about the outside perimeter thereof, such as rib 76, for providing sealing engagement with the interior surface of syringe barrel wall 14. Plunger head 70 is adapted for movement within the interior chamber 20 of syringe barrel 12, with plunger head 70 sliding or riding along the interior surface of syringe barrel wall 14. Such movement is effected through plunger rod 42, as will be discussed further herein. Plunger head 70 may further include a recess 78 in the proximal face at second end 74 for accommodating an interconnection with a plunger rod 42.

The interconnection between plunger head 70 and plunger rod 42 at second end 46 thereof provides for pivoting movement of plunger rod 42 with respect to plunger head 70. This may be accomplished with plunger rod 42 and plunger head 70 being integrally formed through a living hinge, or as separate elements that are attached or otherwise interconnected together. For example, plunger rod 42 may be constructed of a stiff polymeric material, with plunger head 70 formed from a separate silicone or rubberized material that is molded integrally with plunger rod 42, such as through a two-shot molding process, or may be a separate material that is mechanically attached or adhesively fixed to plunger rod 42.

In one embodiment as shown in FIGS. 1A-1D, syringe assembly 10 may further be provided with a connector 80 for interconnecting second end 46 of plunger rod 42 with plunger head 70. With rearward end 18 of syringe barrel 12 being open-ended, such a connector may also serve as a mechanism closing rearward opening 24 of rearward end 18 of syringe barrel 12, thereby providing interior chamber 20 as a closed chamber. Connector 80 includes a hinge 82, which provides a mechanism for pivoting movement of plunger rod 42 with respect to plunger head 70 and the rearward end 18 of syringe barrel 12. Connector 80 may further include an elongated extension 84 that has an outer diameter substantially the same as an inner diameter of recess 78 of plunger head 70, so as to provide an interference fit therein, thereby connecting connector 80 and plunger head 70 together, such as through a mechanical engagement, a biocompatible adhesive, sonic welding, etc. Connector 80 further includes a recessed profile 86 on an external surface thereof for accommodating second end 46 of plunger rod 42 when plunger rod 42 is pivoted to the second position to be in axial alignment with syringe barrel 12, as will be discussed in further detail herein.

In an alternate embodiment, it is further contemplated that hinge 82 may be spring loaded, so as to exert a biasing force in the rearward direction, thereby maintaining a pre-load which biases tip guard 50 into sealing engagement with forward end 16 of syringe barrel 12. It is also contemplated that hinge 82 may include a bias so as to automatically cause plunger rod 42 to pivot from the first position toward the second position upon release of the sealing engagement of tip guard 50 with forward end 16.

Since tip guard 50 completely seals the contents of syringe assembly 10 at forward end 16, syringe assembly 10 can be provided as an integral product without the need for any additional external packaging to maintain sterility. In such an embodiment, it is contemplated that a seal such as a breakable membrane (not shown) be provided at rearward end 18 of syringe barrel 12, to maintain and ensure sterility of the inside of the syringe barrel 12 behind the plunger head 70 during shipping and handling. Such a seal may be adapted to break or tear during use, such as when the plunger rod 42 is pivoted into the second position and locked into recessed profile 86 of connector 80.

Moreover, it may also be desirable to incorporate further anti-tamper features into the syringe assembly 10, such as an anti-tamper mechanism at the forward end 16 that would show whether tip guard 50 has been moved or removed, or otherwise tampered with. Such a feature is particularly useful in embodiments where syringe assembly 10 is provided for use as an integral product without any additional external packaging. Such a feature may include a seal that extends between forward end 16 of syringe barrel 12 and tip guard 50 and can show when tip guard 50 has been moved relative to forward end 16 of syringe barrel 12.

All of the components of syringe assembly 10 may be constructed of any known material, and may be constructed of medical grade polymers. In one preferred embodiment, syringe barrel 12 is constructed of glass, which is particularly useful for containing drugs and medications, since it is fairly inert and well known for use in such applications. When glass is used as the syringe barrel 12, it may be desirable to provide protection for the glass syringe barrel 12, such as a separate plastic tube surrounding the glass syringe barrel, shown as tube 15 in FIGS. 1A-2D (and in particular in FIGS. 1D and 2D), which provides protection from breakage of the glass syringe barrel. This arrangement is particularly useful in embodiments where it is contemplated that the syringe assembly 10 is to be used without any additional external packaging, with the syringe assembly 10 itself including tip guard 50 providing for sterility during delivery and storage prior to use. It is further contemplated that tip guard 50 and plunger rod 42 can provide protection for the glass syringe barrel 12 by offering further support and shielding portions of the glass syringe barrel 12 during storage and transport.

Syringe assembly 10 is particularly useful as a pre-filled syringe, and therefore may be provided for end use with a fluid, such as a medication, contained within interior chamber 20 of syringe barrel 12, pre-filled by the manufacturer. In this manner, syringe assembly 10 can be manufactured, pre-filled with a medication, sterilized, and optionally packaged in separate packaging, for delivery, storage and use by the end user, without the need for the end user to fill the syringe with medication from a separate vial prior to use.

In use, syringe assembly 10 is provided with a medication pre-filled and contained within interior chamber 20 of syringe barrel 12 and with plunger rod 42 in a first position with tip guard 50 adjacent and encompassing forward end 16 of syringe barrel 12, and, in particular, luer tip 28 and luer lock 30. Such engagement provides a mechanism for maintaining sterility of the outer surface of the luer collar at luer lock 30, the luer tip 28, and the interior of syringe barrel 12.

Figure 5:
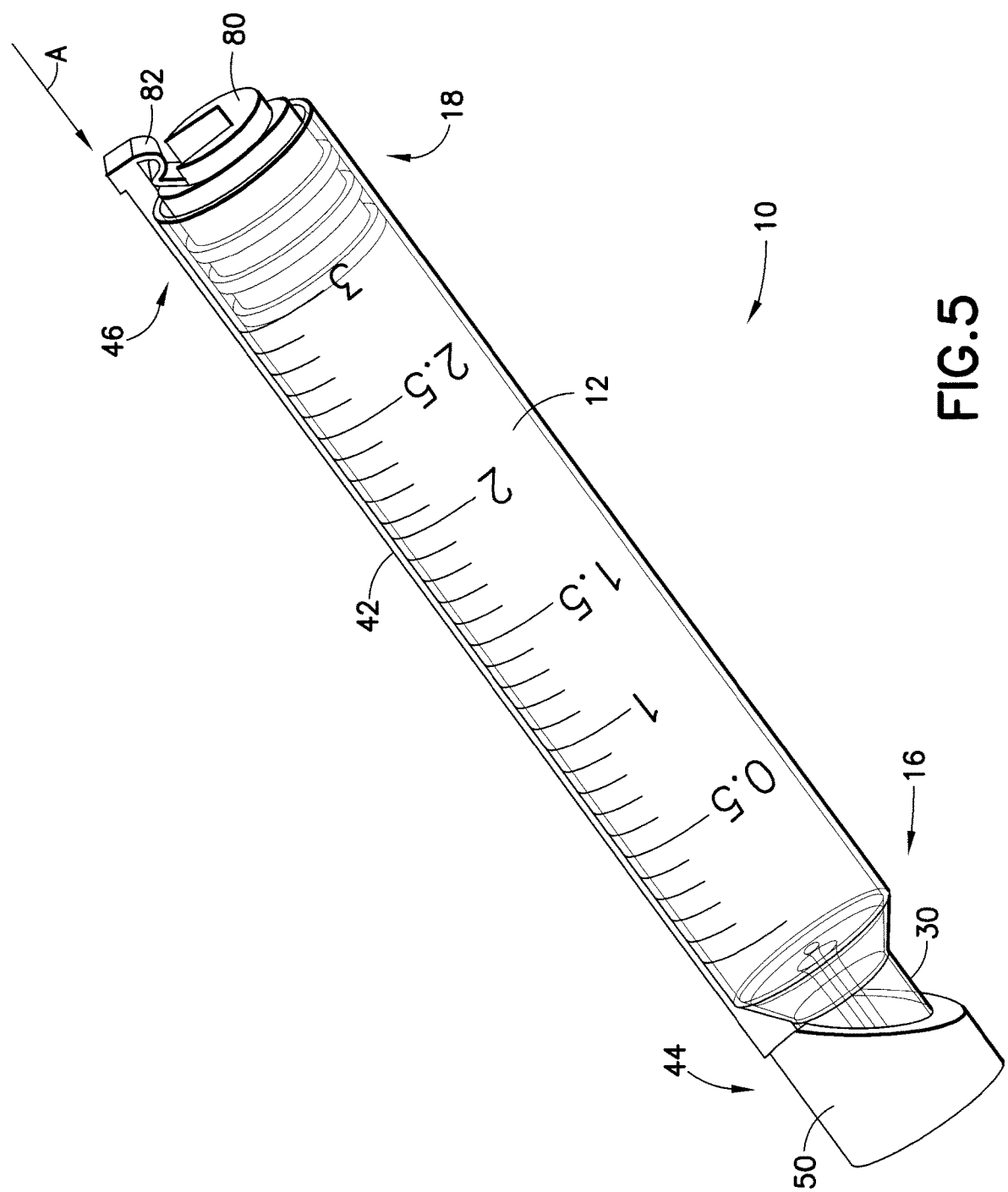
FIGS. 5-8 are perspective views of the syringe assembly of FIG. 3 showing operation of the syringe assembly in an initial state prior to use, during pivoting of the plunger rod, after locking of the plunger rod prior to dispensing of the contents, and after dispensing of the contents, respectively.

In order to release tip guard 50 from forward end 16 of syringe barrel 12, the user exerts pressure on plunger assembly 40 in an axial direction as shown at arrow A in FIG. 5, such as by pushing downward axially on second end 46 of plunger rod 42 and/or by pulling tip guard 50 downward axially away from forward end 16 of syringe barrel 12, such as by the user placing fingertips about opposing sides of tip guard 50 at finger recesses 92. Hinge 82 includes sufficient play so as to permit plunger rod 42 to deflect axially, thereby causing tip guard 50 to move axially away from forward end 16. In one embodiment, it is contemplated that hinge 82 may include a breakable mechanism so as to maintain tip guard 50 in sealed relation with forward end 16 until such breakable connection at hinge 82 permits axial deflection of plunger rod 42. It is further contemplated that plunger assembly 40 includes a bias so as to maintain tip guard 50 about forward end 16 of syringe barrel 12 until such bias is overcome, such as through the downward axial pressure discussed above.

Figure 6:
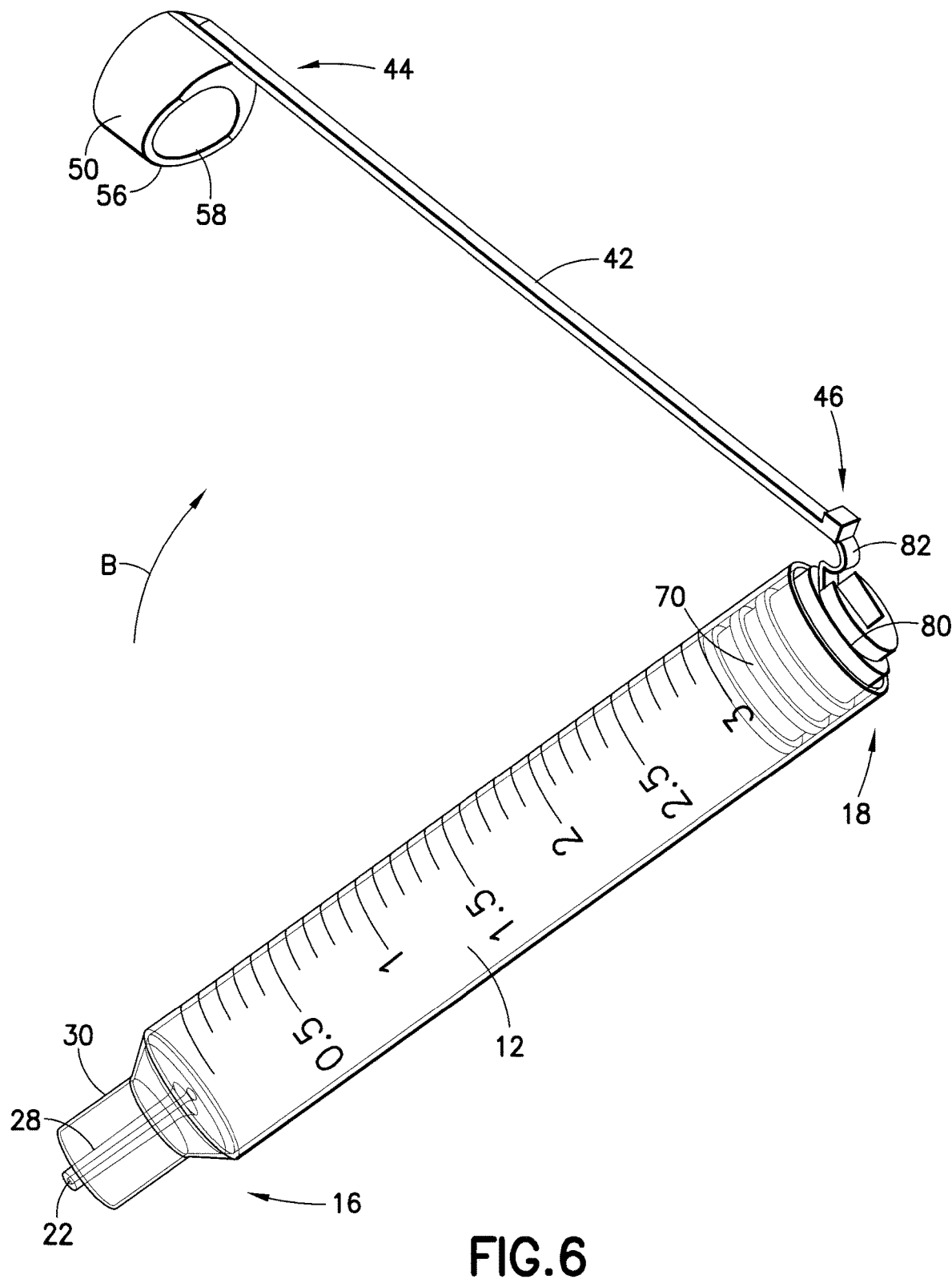
Figure 7:
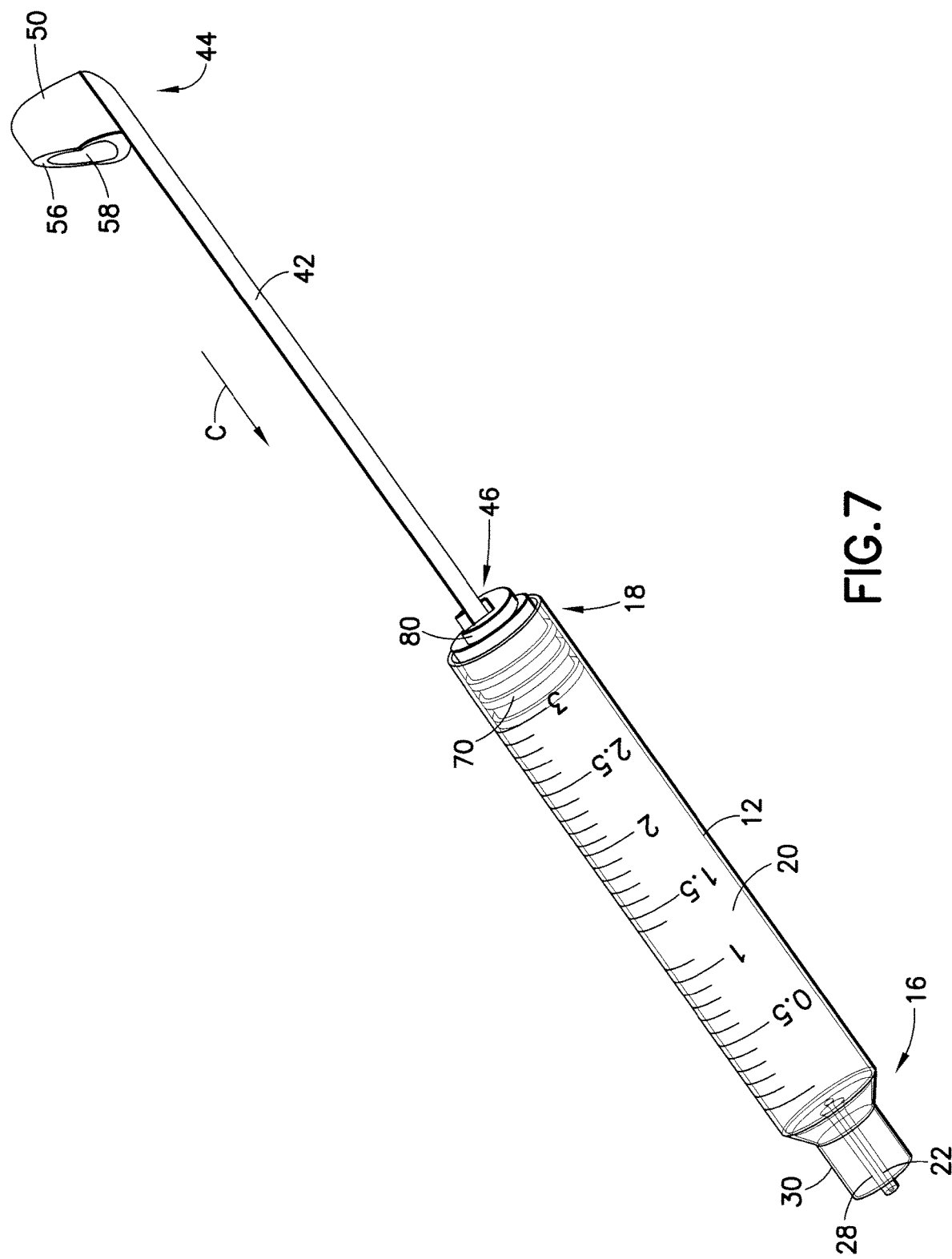

Once tip guard 50 moves a sufficient distance so as to permit annular skirt 56 to clear the end of luer lock 30 and luer tip 28, plunger rod 42 is free for pivotal movement about hinge 82. As shown in FIG. 6, the user can then manually pivot or otherwise move first end 44 of plunger rod 42 in the direction of arrow B about pivot hinge 82 into a second position in which plunger rod 42 is in general axial alignment with syringe barrel 12, as seen in FIG. 7. Such pivoting movement may be accomplished manually by the user. Alternatively or in addition thereto, plunger assembly 40 may include a mechanism for biasing the plunger rod 42 about hinge 82 so as to automatically cause plunger rod 42 to pivot in this manner upon release thereof. Second end 46 of plunger rod 42 may engage within recessed profile 86 of connector 80, so as to lock plunger rod 42 in axial alignment therein.

Syringe assembly 10 can then be grasped with the user's thumb on thumb pad 52 of tip guard 50, and with the user's fingers extending between finger flanges 90a and 90b (shown in FIG. 9). In this manner, syringe assembly 10 is grasped by the user in a well known and well recognized manner.

Prior to the dispensing of medication, any air trapped within interior chamber 20 can be expelled by initial movement of plunger rod 42 into syringe barrel 12 in a known manner. The user can attach luer tip 28 to a separate needle assembly or IV connection assembly and lockingly engage through threads 32 of luer lock 30 in a known manner. When it is desired to deliver the medication, the user effects a squeezing movement between the thumb and forefingers, thereby depressing plunger rod 42 into the open rearward end 18 of syringe barrel 12 in the direction of arrow C shown in FIG. 7. Such movement transfers to plunger head 70 thereby causing movement of plunger head 70 within interior chamber 20 of syringe barrel 12, reducing the volume of interior chamber 20, and creating a positive pressure therein.

Since interior chamber 20 is sealed to the external environment through plunger head 70, the medication fluid within interior chamber 20 is forced out through outlet opening 22 at forward end 16 of syringe barrel 12. In this manner, the fluid medication can be expelled from the syringe barrel 12 through outlet opening 22, and into the separate needle assembly or IV assembly and into the patient.

Figure 8:
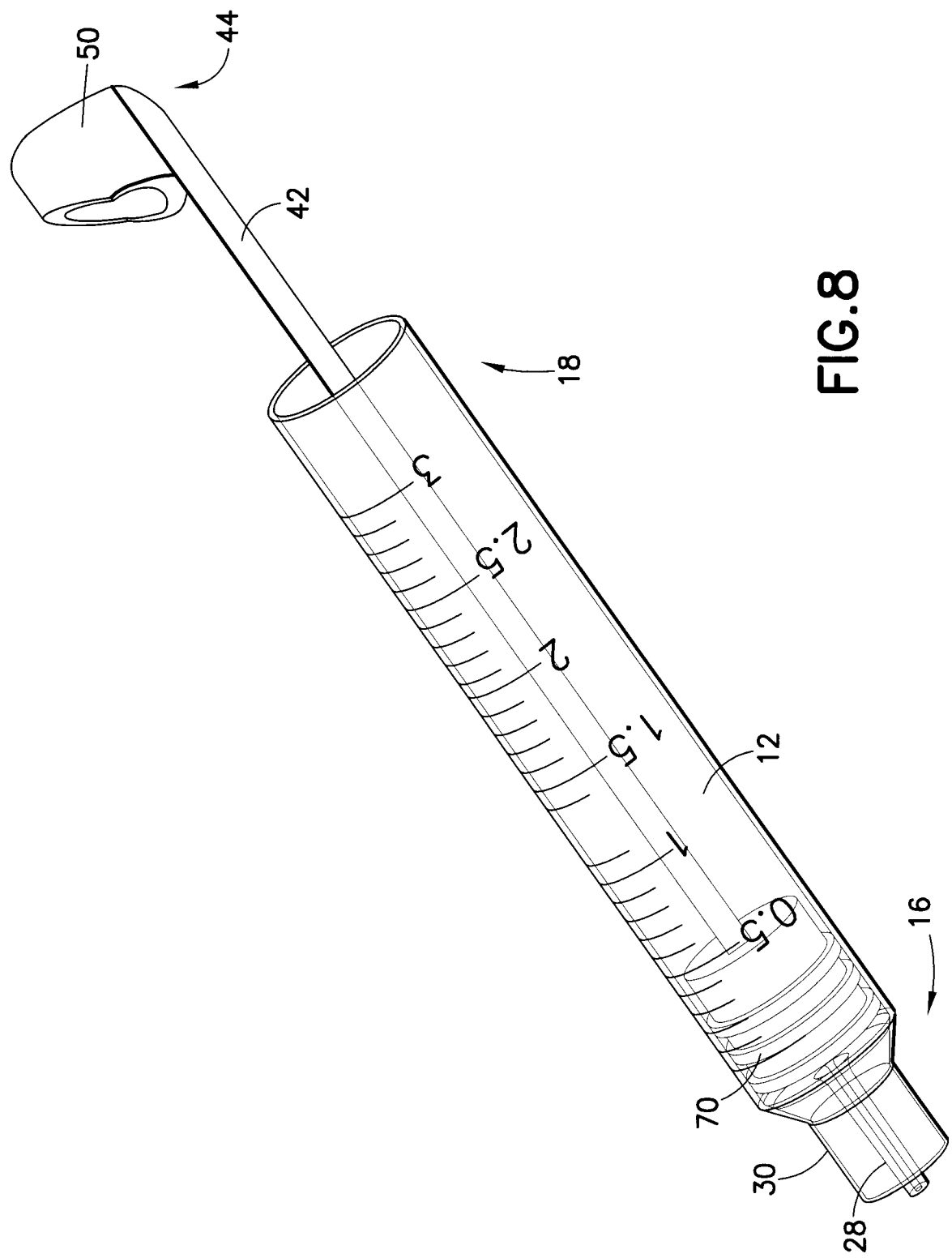

Upon full movement of plunger head 70 through syringe barrel 12, plunger head 70 "bottoms out", as shown in FIG. 8. At this point, syringe assembly 10 can be removed from the patient and appropriately discarded. It is further contemplated that plunger rod 42 may incorporate a fracturable connection, such as at hinge 82, so that any attempt to retract plunger rod 42 out of syringe barrel 12 for re-use, will cause hinge 82 to fracture and disconnect from connector 80 and plunger head 70.

Syringe assembly 10 can be filled with a fluid in a variety of ways. In one non-limiting example, tip guard 50 is placed over outlet opening 22 to thereby cover outlet opening 22 and provide a barrier preventing the flow of fluid contained within interior chamber 20 of syringe barrel 12 through outlet opening 22. Once a barrier is in place at the outlet opening 22, fluid can be added to the interior chamber 20 of syringe barrel 12 through rearward opening 24 at rearward end 18 of syringe barrel 12. When filling syringe assembly 10 in this manner, plunger head 70 and plunger rod 42 should not be disposed within interior chamber 20. Plunger head 70 may be assembled within interior chamber 20 under a vacuum environment, or through the use of a vent tube, so as to prevent any increase in pressure within interior chamber 20 during plunger head insertion. After filling is complete, plunger head 70 can be positioned within interior chamber 20. If plunger head 70 is interconnected with tip guard 50 through plunger rod 42 and connector 80, or through plunger rod 42 alone, the interconnection mechanism between plunger rod 42 and plunger head 70 is provided with sufficient play to permit plunger head 70 to be inserted into interior chamber 20 of syringe barrel 12 through rearward opening 24 at rearward end 18 while maintaining the position of tip guard 50 at the forward end 16.

In another non-limiting embodiment, syringe assembly 10 can be filled with a fluid by injecting the fluid through the outlet opening 22. In this arrangement, plunger head 70 is fitted into interior chamber 20 of syringe barrel 12 and positioned to the fully bottomed out position. Fluid is then added through outlet opening 22 at the forward end 16. As the fluid enters interior chamber 20 through outlet opening 22, plunger head 70 is pushed away from forward end 16 and toward rearward end 18 based on the pressure of the fluid entering interior chamber 20. After the desired volume of fluid is filled, plunger rod 42 can be interconnected with plunger head 70 (if it has not already been connected thereto). The tip guard 50 may then be fitted over forward end 16 of the syringe assembly 10 to form a closed interior chamber. This filling operation may be performed under aseptic conditions, or the syringe assembly can be terminally sterilized after the syringe is sealed with tip guard 50 thereover.

Figure 11:
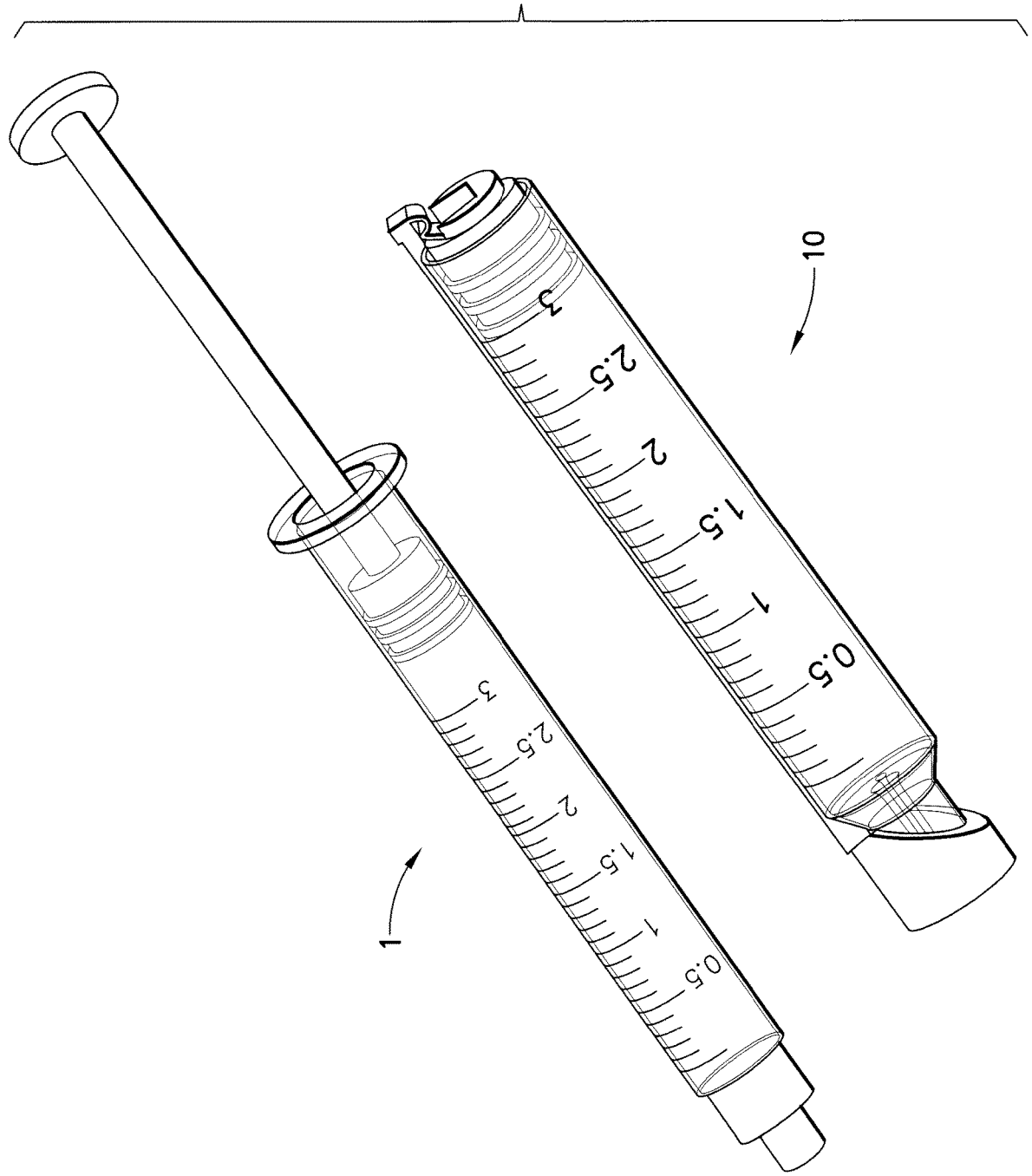
FIG. 11 is a perspective view comparing a conventional syringe to a syringe assembly in accordance with the present invention.

With such an arrangement, the overall size and shape of syringe assembly 10 when filled for use is of an overall profile similar to a conventional syringe after use with a plunger completely extended within a syringe barrel, as seen in FIG. 11, which depicts the profile of a conventional syringe 1 in comparison to syringe assembly 10 in accordance with the present invention. As such, the profile is significantly reduced from that of a conventional pre-filled syringe, which includes the plunger retracted from the barrel prior to use. In addition, by incorporating a tip guard into the movable plunger rod, a device is achieved that not only reduces the overall profile for packaging, but also maintains sterility due to the engagement of the tip guard based on the movement of the plunger rod, which is the mechanism for reduced profile. In this manner, the need for separate packaging to maintain sterility is reduced or eliminated.

What is claimed is:

1. A syringe assembly, comprising:
   a syringe barrel having an inside surface defining a chamber, an open proximal end, and a distal end;
   an elongated plunger rod extending between a first end and a second end;
   a guard disposed on the first end of the plunger rod; and
   a plunger head extending within the chamber of the syringe barrel, the second end of the plunger rod interconnected with the plunger head through a pivotable connection,
   wherein the plunger head is adapted for slidable movement within the syringe barrel between the proximal end and the distal end,
   wherein the plunger rod is adapted to pivot with respect to the plunger head between a first position in which the guard is adjacent the distal end of the syringe barrel and a second position in which the plunger rod is in general axial alignment with the syringe barrel, and is further adapted for axial movement so as to cause said slidable movement of the plunger head through the syringe barrel,
   wherein the guard is adapted to cover at least the distal end of the syringe barrel when the plunger rod is in the first position, wherein the guard comprises an annular skirt forming an opening which surrounds the distal end of the syringe barrel in the first position, and wherein the pivotal connection is configured such that the guard may be freed from the distal end of the syringe barrel by application of a distally directed axial force to the plunger rod allowing the annular skirt to move distally beyond the distal end of the syringe barrel thereby allowing the plunger rod to pivot to the second position.

2. The syringe assembly of claim 1, wherein the guard is integrally formed with the plunger rod.

3. The syringe assembly of claim 1, wherein the guard comprises at least one tactile surface along an outer surface thereof, wherein the tactile surface includes a textured portion.

4. The syringe assembly of claim 3, wherein the tactile surface comprises at least one recess formed in the outer surface of the guard.

5. The syringe assembly of claim 1, wherein the distal end of the syringe barrel includes an opening adapted for engagement with a needle assembly or an IV connection assembly.

6. The syringe assembly of claim 1, wherein the annular skirt forms a generally cylindrical opening.

7. The syringe assembly of claim 6, wherein the distal end of the syringe barrel comprises an engagement mechanism extending therefrom, and the generally cylindrical opening is configured to surround the engagement mechanism.

8. The syringe assembly of claim 7, wherein the engagement mechanism comprises a luer tip.

9. The syringe assembly of claim 8, wherein the engagement mechanism further comprises a luer lock.

10. The syringe assembly of claim 6, wherein the generally cylindrical opening comprises a sealing material.

11. The syringe assembly of claim 6, wherein the annular skirt comprises a cut-away section providing the guard with a reduced profile about a section of the annular skirt.

12. The syringe assembly of claim 6, wherein the annular skirt is comprised of a plurality of sections which snap fit together.

13. The syringe assembly of claim 1, wherein the plunger rod is adapted to pivot with respect to the plunger head between the first position and the second position by way of a hinge.

14. The syringe assembly of claim 13, wherein the hinge is a living hinge.

15. The syringe assembly of claim 14, wherein the plunger rod and the plunger head are integrally formed, and the living hinge interconnects the second end of the plunger rod with the plunger head.

16. The syringe assembly of claim 13, wherein the hinge is adapted to provide a biasing force on the plunger rod.

17. The syringe assembly of claim 16, wherein the biasing force biases the plunger rod toward the first position.

18. The syringe assembly of claim 16, wherein the biasing force biases the plunger rod toward the second position.

19. The syringe assembly of claim 1, further comprising a connector at least partially extending into the open proximal end of the syringe barrel, wherein the connector interconnects the second end of the plunger rod with the plunger head.

20. The syringe assembly of claim 19, wherein the connector comprises a hinge which provides for pivoting movement of the plunger rod with respect to the plunger head.

21. The syringe assembly of claim 19, wherein the connector comprises a recessed portion for accommodating the second end of the plunger rod when the plunger rod is pivoted to the second position.

22. The syringe assembly of claim 19, wherein the connector is adapted to close the open proximal end of the syringe barrel.

23. The syringe assembly of claim 19, wherein the connector comprises an elongated extension portion that extends into a recess formed in the plunger head.

24. The syringe assembly of claim 1, wherein the pivotable connection between the plunger rod and the plunger head is fracturable.

25. A syringe assembly, comprising:
    a syringe barrel having an inside surface defining a chamber, an open proximal end, and a distal end;
    an elongated plunger rod extending between a first end and a second end;
    a guard disposed on the first end of the plunger rod; and
    a plunger head extending within the chamber of the syringe barrel, the second end of the plunger rod interconnected with the plunger head through a pivotable connection,
    wherein the guard is positioned to cover at least the distal end of the syringe barrel, wherein the guard comprises an annular skirt forming an opening which surrounds the distal end of the syringe barrel in the first position, and wherein the pivotal connection is configured such that the guard may be freed from the distal end of the syringe barrel by application of a distally directed axial force to the plunger rod allowing the annular skirt to move distally beyond the distal end of the syringe barrel thereby allowing the plunger rod to pivot to the second position.

26. The syringe assembly of claim 25, wherein the annular skirt forms a generally cylindrical opening.

27. The syringe assembly of claim 26, wherein the generally cylindrical opening surrounds an engagement mechanism extending from the distal end of the syringe barrel.

28. The syringe assembly of claim 25, further comprising an anti-tamper seal adapted to be ruptured when the plunger rod is pivoted from a first position.

29. The syringe assembly of claim 28, wherein the anti-tamper seal is provided at the proximal end of the syringe barrel.

30. The syringe assembly of claim 28, wherein the anti-tamper seal is provided at the distal end of the syringe barrel.

31. The syringe assembly of claim 25, wherein the chamber is at least partially filled with a fluid.

32. The syringe assembly of claim 25, wherein the distal end of the syringe barrel includes an opening adapted for engagement with a needle assembly or an IV connection assembly.

33. A method of dispensing a fluid, comprising:
providing a syringe assembly comprising:
a syringe barrel having an inside surface defining a chamber containing the fluid, an open proximal end, and a distal end;
an elongated plunger rod extending between a first end and a second end;
a guard disposed on the first end of the plunger rod, wherein the plunger rod is in a first position in which the guard is covering at least the distal end of the syringe barrel; and
a plunger head extending within the chamber of the syringe barrel, the second end of the plunger rod interconnected with the plunger head through a pivotable connection, wherein the guard comprises an annular skirt forming an opening which surrounds the distal end of the syringe barrel in the first position, and wherein the pivotal connection is configured such that the guard may be freed from the distal end of the syringe barrel by application of a distally directed axial force to the plunger rod allowing the annular skirt to move distally beyond the distal end of the syringe barrel thereby allowing the plunger rod to pivot to the second position;
pivoting the plunger rod from the first position to a second position in which the plunger rod is in general axial alignment with the syringe barrel; and
depressing the plunger rod into the open proximal end of the syringe barrel to cause movement of the plunger head through the syringe barrel.

34. The method of dispensing a fluid of claim 33, wherein the distal end of the syringe barrel includes an opening adapted for engagement with a needle assembly or an IV connection assembly.

* * * * *